US008382730B2

(12) United States Patent
Tauer

(10) Patent No.: US 8,382,730 B2
(45) Date of Patent: Feb. 26, 2013

(54) SURGICAL FLUID BASIN

(75) Inventor: Mark Tauer, Belchertown, MA (US)

(73) Assignee: Covidien LP, Mansfield, MA (US)

( * ) Notice: Subject to any disclaimer, the term of this patent is extended or adjusted under 35 U.S.C. 154(b) by 523 days.

(21) Appl. No.: 11/705,981

(22) Filed: Feb. 14, 2007

(65) Prior Publication Data
US 2008/0202969 A1    Aug. 28, 2008

(51) Int. Cl.
A61M 1/00    (2006.01)
G01F 19/00   (2006.01)

(52) U.S. Cl. ......... 604/317; 73/426; 73/427; 206/459.1; 206/459.5; 206/505; 206/510; 206/515; 206/518; 220/669; 220/560.03; 220/4.21; 220/4.24; 220/4.25; 220/4.26; 220/660; 220/670; 220/671; 220/672; 220/673; 220/674; 220/755; 220/DIG. 13; 220/DIG. 25

(58) Field of Classification Search ................ 604/317; 206/515, 505, 510, 503, 518, 495.5, 459.5, 206/459.1; 220/560.03, 4.21, 4.24, 4.25, 220/4.26, 660, 755, DIG. 13, DIG. 25, 669–675; 73/426, 427

See application file for complete search history.

(56) References Cited

U.S. PATENT DOCUMENTS

| | | | | | |
|---|---|---|---|---|---|
| 343,510 | A | * | 6/1886 | Welsh | 73/427 |
| 423,018 | A | * | 3/1890 | Young | 73/427 |
| D46,262 | S | | 8/1914 | Meinecke | |
| 1,331,372 | A | * | 2/1920 | Popper | 220/669 |
| 1,507,968 | A | * | 9/1924 | Johnson | 73/427 |
| 1,564,470 | A | * | 12/1925 | Crimmel | 73/427 |
| 1,718,897 | A | * | 6/1929 | Scholes et al. | 222/158 |
| 2,208,431 | A | * | 7/1940 | Rochow | 366/130 |
| D158,985 | S | * | 6/1950 | Lorenzen | D24/123 |
| 2,526,602 | A | * | 10/1950 | Crumrine | 206/305 |
| D211,047 | S | * | 5/1968 | Johnson | D10/46.2 |
| D213,534 | S | * | 3/1969 | Cavenah | D24/204 |
| D216,058 | S | | 11/1969 | Painter et al. | |
| D217,409 | S | | 4/1970 | Ott | |
| D219,323 | S | | 11/1970 | Bost | |
| 3,992,729 | A | | 11/1976 | Mills | |
| 4,080,968 | A | | 3/1978 | Nielsen | |
| D249,162 | S | | 8/1978 | Mills | |
| 4,368,548 | A | | 1/1983 | Glass | |
| D269,378 | S | | 6/1983 | Work | |
| 4,416,381 | A | * | 11/1983 | Swartwout | 215/228 |
| D275,606 | S | | 9/1984 | Zawachi | |
| 4,474,016 | A | | 10/1984 | Winchell | |
| 4,616,642 | A | | 10/1986 | Martin et al. | |
| 4,925,047 | A | * | 5/1990 | Valentine et al. | 220/23.83 |
| 5,045,076 | A | | 9/1991 | Pierce | |
| 5,072,832 | A | * | 12/1991 | Valentine et al. | 206/570 |
| 5,201,893 | A | * | 4/1993 | Holloway et al. | 206/571 |

(Continued)

Primary Examiner — Tatyana Zalukaeva
Assistant Examiner — Ginger T Chapman
(74) Attorney, Agent, or Firm — Lisa E. Winsor, Esq.

(57) ABSTRACT

A surgical fluid basin includes a receptacle member having a lower wall and a peripheral wall extending from the lower wall and arranged about a longitudinal axis, and having an internal chamber within the peripheral wall for reception of fluids. The peripheral wall has at least one terrace defined within the peripheral wall corresponding to a volume of fluid contained within the internal chamber. The at least one terrace defines an internal rise surface and an internal run surface intersecting the internal rise surface. The internal run surface includes indicia markings corresponding to the volume of fluid contained within the internal chamber. A plurality of terraces may be defined within the peripheral wall with each terrace corresponding to a predetermined volume of fluid contained within the internal chamber. The internal run surface defined by each terrace includes indicia markings corresponding to the volume of fluid contained within the internal chamber.

8 Claims, 6 Drawing Sheets

U.S. PATENT DOCUMENTS

| | | | |
|---|---|---|---|
| 5,381,901 A * | 1/1995 | Hundley | 206/457 |
| 5,397,036 A * | 3/1995 | Maiwald | 222/475 |
| 5,487,393 A | 1/1996 | Haswell et al. | |
| 5,674,227 A | 10/1997 | Burns | |
| 5,697,921 A | 12/1997 | Blair | |
| D412,448 S * | 8/1999 | Bentson | D10/46.2 |
| 6,044,650 A * | 4/2000 | Cook et al. | 62/130 |
| D441,075 S | 4/2001 | Nara | |
| 6,238,907 B1 | 5/2001 | Schuler-Maloney et al. | |
| 6,398,062 B1 | 6/2002 | Jones | |
| 6,415,455 B1 | 7/2002 | Slaon, III et al. | |
| 6,532,604 B2 | 3/2003 | Moser | |
| 6,543,284 B2 * | 4/2003 | Hoeting et al. | 73/427 |
| 6,602,230 B1 | 8/2003 | Fisher et al. | |
| 6,622,864 B1 * | 9/2003 | Debbs et al. | 206/438 |
| D482,780 S | 11/2003 | Robbins et al. | |
| 6,769,302 B1 * | 8/2004 | King et al. | 73/427 |
| 7,025,733 B2 | 4/2006 | McQuaid | |
| 7,048,317 B2 * | 5/2006 | Netsch | 294/180 |
| 7,086,552 B2 * | 8/2006 | Zepter | 220/573.4 |
| 7,147,626 B2 | 12/2006 | Goodman et al. | |
| 7,153,294 B1 | 12/2006 | Farrow | |
| D548,115 S * | 8/2007 | Sawhney et al. | D10/46.2 |
| 7,306,120 B2 * | 12/2007 | Hughes | 222/158 |
| D597,203 S * | 7/2009 | Tauer | D24/121 |
| 2003/0155262 A1* | 8/2003 | Graham | 206/459.5 |
| 2005/0011261 A1* | 1/2005 | Lyon | 73/427 |
| 2005/0197638 A1 | 9/2005 | Papendick et al. | |
| 2006/0009742 A1 | 1/2006 | Solazzo | |
| 2006/0029695 A1* | 2/2006 | Kaczor | 426/87 |
| 2007/0068250 A1* | 3/2007 | Krent | 73/427 |
| 2009/0255333 A1* | 10/2009 | Henry et al. | 73/427 |

* cited by examiner

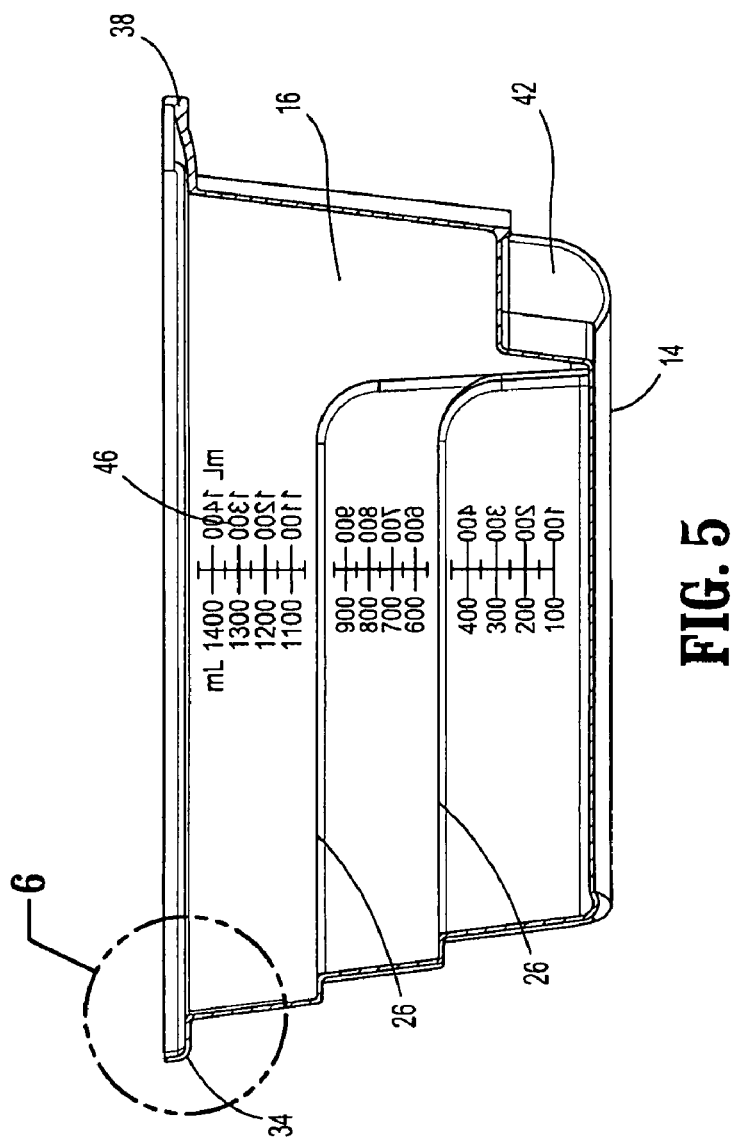
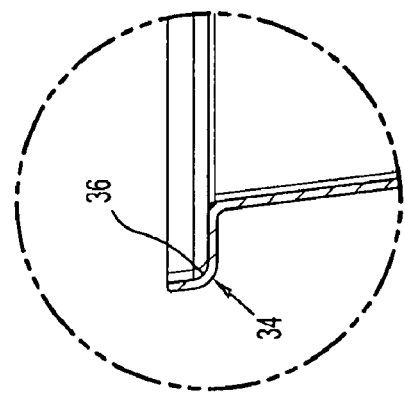
FIG. 5
FIG. 6

SURGICAL FLUID BASIN

BACKGROUND

1. Technical Field

The present disclosure generally relates to fluid containers for use in medical care, and, more specifically, relates to a disposable fluid basin intended for use in conjunction with a medical procedure and having functional features which, e.g., facilitate the determination of the volume of fluid contained within the fluid basin and enhance its structural integrity.

2. Related Art

Fluid basins for accumulating body fluids, irrigation fluids, tissue or the like in the course of performing a surgical procedure are known in the art. These basins are normally formed of stainless steel or may be molded from a suitable polymeric material. Conventional fluid basins have various design characteristics which are generally aesthetic in nature. Some of the more popular designs include circular or kidney-shaped.

Various disadvantages with conventional fluid basins are evident. The inability of the clinician to readily ascertain the volume of fluid within the basin is one issue which, when presented, may result in spillage or overflow within the surgical site. In addition, the overall structural instability of some of the polymeric basins may be problematic particularly during handling of a full basin.

SUMMARY

Accordingly, the present disclosure is directed to a surgical fluid basin apparatus. The fluid basin apparatus includes a receptacle member having a lower wall and a peripheral wall extending from the lower wall and arranged about a longitudinal axis. The receptacle member has an internal chamber within the peripheral wall for reception of fluids. The peripheral wall has at least one terrace defined within the peripheral wall. The at least one terrace corresponds to a volume of fluid contained within the internal chamber. The at least one terrace defines an internal rise surface and an internal run surface intersecting the internal rise surface. The internal run surface includes indicia markings corresponding to the volume of fluid contained within the internal chamber.

In one embodiment, a plurality of terraces may be defined within the peripheral wall with each terrace corresponding to a predetermined volume of fluid contained within the internal chamber. The internal run surface of each terrace includes indicia markings corresponding to the volume of fluid contained within the internal chamber. At least three terraces may be within the peripheral wall. The terraces may be arranged to correspond to substantially equal incremental increases of the volume of fluid contained within the chamber. The terraces may be dimensioned to increase the structural integrity of the peripheral wall.

The peripheral wall may include an outer lip remote from the lower wall. Secondary gradation markings may be disposed on a wall surface of the peripheral wall to provide visual indicia regarding the volume of fluid in the container. The peripheral wall may be at least partially translucent or fully translucent.

The receptacle member may be generally heart-shaped defining two curve segments extending to a cusp segment. The cusp segment is generally recessed. The cusp segment may be inclusive of the terraces whereby the indicia markings corresponding to the volume of fluid contained within the internal chamber are within the cusp segment on respective run surfaces of the terraces. The cusp segment may be dimensioned to increase surface area of the respective run surfaces of the terraces to accommodate the indicia markings.

In another embodiment, a surgical fluid basin includes a receptacle member having a lower wall and a peripheral wall extending from the lower wall and arranged about a longitudinal axis, and having an internal chamber within the peripheral wall for reception of fluids. The peripheral wall includes a plurality of terraces defined within the peripheral wall. Each terrace corresponds to a volume of fluid contained within the internal chamber, and has indicia markings to indicate to the clinician the volume of fluid.

BRIEF DESCRIPTION OF THE DRAWINGS

Preferred embodiments of the disclosure will be better appreciated by reference to the drawings wherein:

FIG. 5 is a side plan view of the surgical fluid basin; and

FIG. 6 is an isolated view of the area of detail identified in FIG. 5 and in cross-section.

DETAILED DESCRIPTION

Figure 1:
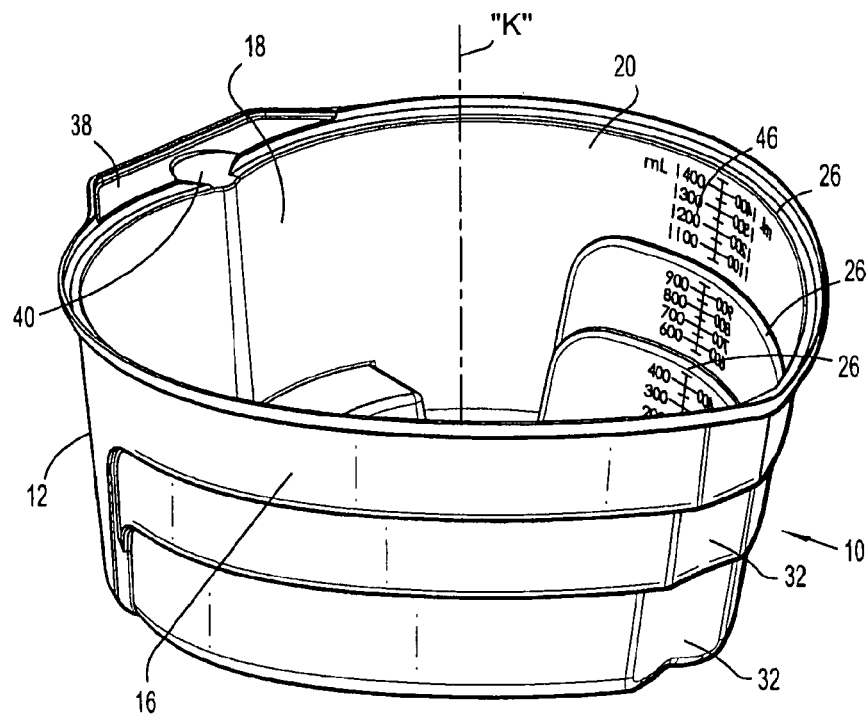
FIGS. 1-2 are perspective views of the surgical fluid basin in accordance with the principles of the present disclosure illustrating the receptacle member, peripheral wall and the terraces within the peripheral wall.
Figure 2:
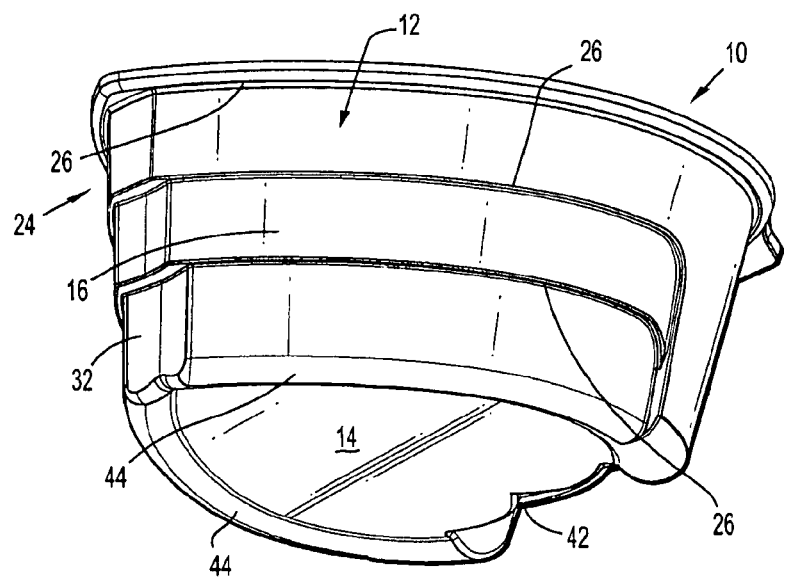

Referring now to the drawings wherein like reference numerals identify similar or like elements throughout the several views, FIGS. 1-2 illustrate, each in perspective view, the surgical fluid basin in accordance with the principles of the present disclosure. Surgical fluid basin 10 is intended to accumulate or collect saline, blood, urine, irrigation fluids, exudates, saliva or the like which may be presented during the performance of a medical or surgical procedure. Such elements will be hereinafter collectively referred to as "fluids". Surgical fluid basin 10 may also accommodate various tissue or organs removed during the procedure.

Surgical fluid basin 10 may be manufactured from stainless steel, aluminum or alloys thereof, or, alternatively, of a suitable polymeric material formed by any known manufacturing, molding, or processing techniques. Several molding techniques include thermal molding or rotational molding, or any other known injection molding technique. Examples of suitable polymeric materials include polycarbonates, polystyrenes, polyacrylates, polypropylene or polyethylene. As a further alternative, surgical fluid basin 10 may be formed of natural biogenic polymers such as cellulose and may be biodegradable. In one embodiment, surgical fluid basin 10 is translucent at least through a portion of the basin 10. Surgical fluid basin 10 is preferably disposable, i.e., is intended to be disposed after a single use; however, it is envisioned that the surgical fluid basin 10 may be sterilized after each use if formed of a suitable sterilizable metal material.

Referring now to FIGS. 1-4, surgical fluid basin 10 includes receptacle member 12 having lower wall 14 and outer peripheral wall 16 extending contiguously from the lower wall 14 and being arranged about longitudinal axis "k". Receptacle member 12 defines internal chamber 18 defined within the boundaries of lower wall 14 and peripheral wall 16. Internal chamber 18 opens at mouth 20 remote from the lower wall 14. Surgical fluid basin 10 may be of various configurations or shapes. In one embodiment, surgical fluid basin 10 is generally heart-shaped when viewed from the top (FIG. 3) having arcuate or curved peripheral side wall segments 22 which meet at cusp wall segment 24. The significance of the various segments will be discussed in greater detail hereinbelow.

Figure 4:
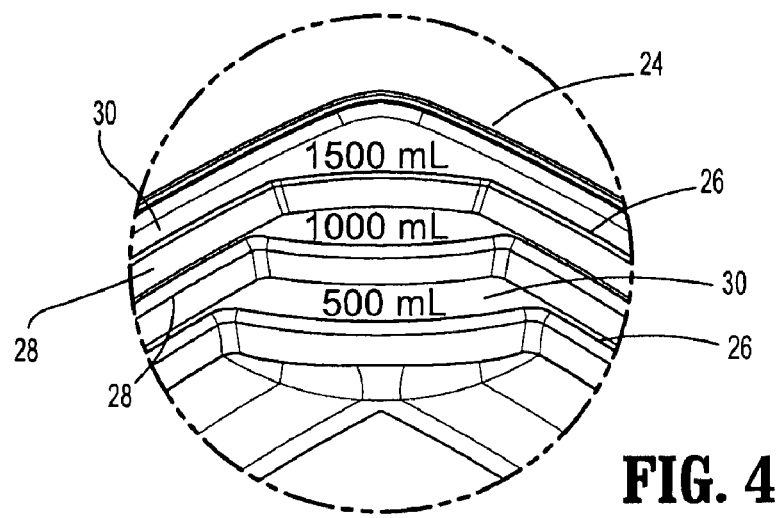
FIG. 4 is an isolated view of the area of detail identified in FIG. 3 illustrating the written indicia on the terraces.

Peripheral wall 16 has at least one, preferably, a plurality of steps or terraces 26 formed within the peripheral wall 16. As best depicted in FIG. 4, each terrace 26 is defined at the intersection of corresponding rise and run surfaces 28, 30 of peripheral wall 16. Each rise surface 28 may extend in the general direction of the longitudinal axis "k" (e.g., vertically directed), and may be parallel or in oblique relation to the longitudinal axis "k". Each run surface 30 may extend in general transverse relation (including perpendicular and oblique) to the longitudinal axis "k" (e.g., horizontally directed) to provide the stepped appearance. Each terrace 26 corresponds to a predetermined volume of fluid contained within receptacle member 12. Specifically, when the fluid within receptacle member approaches, approximates or becomes level with a respective terrace 26, the clinician is aware of the corresponding volume of fluid with the receptacle member 12 by viewing internal chamber 18. The fluid level within internal chamber 18 may be viewed by looking downward within the internal chamber 18. In addition, in instances where the clinician is not next to receptacle member 12, the arrangement of terraces 26 permits the clinician to obtain a quick and generally accurate estimation of the fluid level from areas, e.g., across the operating room. In one embodiment, terraces 26 are arranged to correspond to incremental increases in volume, e.g., at increments of 500 milliliters (mls). Other arrangements are envisioned as well. In addition, each terrace 26 extends for only a peripheral portion of peripheral wall 16.

Each terrace 26 may have indicia markings including written indicia corresponding to the predetermined fluid volume. The written indicia may be in the form of numerical and/or text symbols, visual symbols or the like, which are written, drawn, engraved or molded into each run surface 30 adjacent a respective terrace 26. In one embodiment, terraces 26 are located to correspond to incremental volume increases of 500 ml. Thus, the lower most terrace 26 closest to lower wall 14 has the symbol "500 ml" noted thereon, the middle terrace has "1000 ml" noted thereon and the upper most terrace has "1500 ml" thereon.

Figure 3:
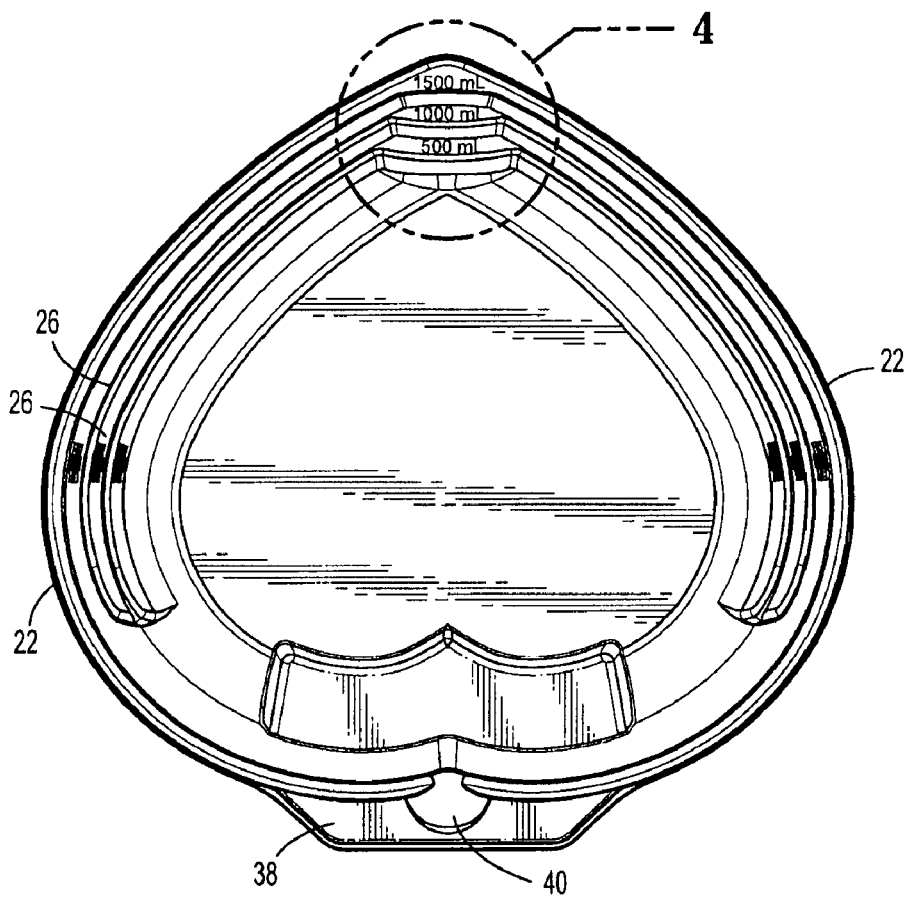
FIG. 3 is a top plan view of the surgical fluid basin illustrating the terraces.

With continued reference to FIGS. 1-4, cusp wall segment 24 is characterized by having a plurality of recessed wall surfaces 32. In particular, recessed wall surfaces 32 do not follow the paths of curved wall segments 22, but, rather define a "recess" or "pushed in" appearance to peripheral wall 16. As illustrated in FIGS. 3 and 4, each run surface 30 includes a central portion and side portions on opposite sides of the central portion. Each side portion has a substantially uniform width that is substantially equal to the uniform width of the opposing side portion and less than the width of the central portion. The central portion of each run surface 30 corresponds to the cusp wall segment 24 and the recessed wall surfaces 32. Recessed wall surfaces 32 perform several functions including: 1) increasing the structural support of receptacle member 12 to enhance its transverse and carrying strength; 2) providing an area for engagement by the clinician for transport; and 3) increasing the surface area of the respective run surfaces 30 adjacent terraces 26 to accommodate the written indicia (see FIG. 4).

Referring now to FIGS. 5-6, in conjunction with FIG. 1, receptacle member 16 further includes outer peripheral lip 34 defined adjacent mouth 18 and uppermost terrace 26. Outer peripheral lip 34 provides increased structural support to receptable member 16 and also provides a fluid overflow to assist in preventing spillage. Outer lip 34 may have a recessed or sloped surface adjacent thereto to define a gully 36 to assist in collecting fluid overflow. As best depicted in FIGS. 1 and 3, receptacle member 16 further includes handle segment 38 diametrically opposed to cusp segment 24. Handle segment 38 may define recess or depression 40. Recess 40 is of generally the same thickness as neighboring areas of handle segment 38. Recess 40 increases the structural integrity of handle segment 38. Recess 40 also may receive the clinician's thumb or any other finger during manipulation of fluid basin 10. Handle 38 is dimensioned to be engaged with one hand of the clinician and, in conjunction with cusp segment 24, which is engaged by the other hand of the clinician, provides a structural means by which to transport surgical fluid basin 10 about the surgical site.

With reference now to FIG. 2, lower wall 14 may have cavity 42 in general alignment with handle segment 38. Cavity 42 may provide an area or receptacle to receive the clinician's hand to enable the clinician to lift fluid basin 10 off a horizontal surface, or, to facilitate transport or pouring of the liquid from fluid basin 10. Lower wall 14 may further include rounded or arcuate peripheral surfaces 44. Peripheral surfaces 44 support receptacle member 12 when the receptacle member 12 is positioned on a surface, and may space lower wall 14 from the surface. Peripheral surfaces 44 also increase the structural integrity of lower wall 14.

Referring now to FIGS. 1 and 5, receptacle member 16 further includes a set of gradation marks or indicia 46 on at least one or both of the surfaces of curved segments 22. Gradation marks 46 run along the longitudinal axis "k", e.g., vertically, of the receptable member 16 to provide an alternate or supplemental means to identify the volume of fluid within the receptable member 16. In one embodiment, the areas of curved segments 22 containing gradation markings 46 of receptacle member 16 are translucent or transparent to permit the clinician to view through the side of receptable member 16 to ascertain the fluid level corresponding to the gradation marking. In a further alternative, the entire receptacle member 16 may be transparent or translucent. Gradation markings 46 may be disposed on the inner or outer surfaces of curved segments 22 and may be printed on, etched or molded into receptable member 16. Gradation marks 46 may be in increments, e.g., in 100 ml increments as shown. Thus, gradation markings 42 enable the clinician to determine fluid volume level in receptable member 10 by viewing through the side of curved segments 22.

Figure 7:
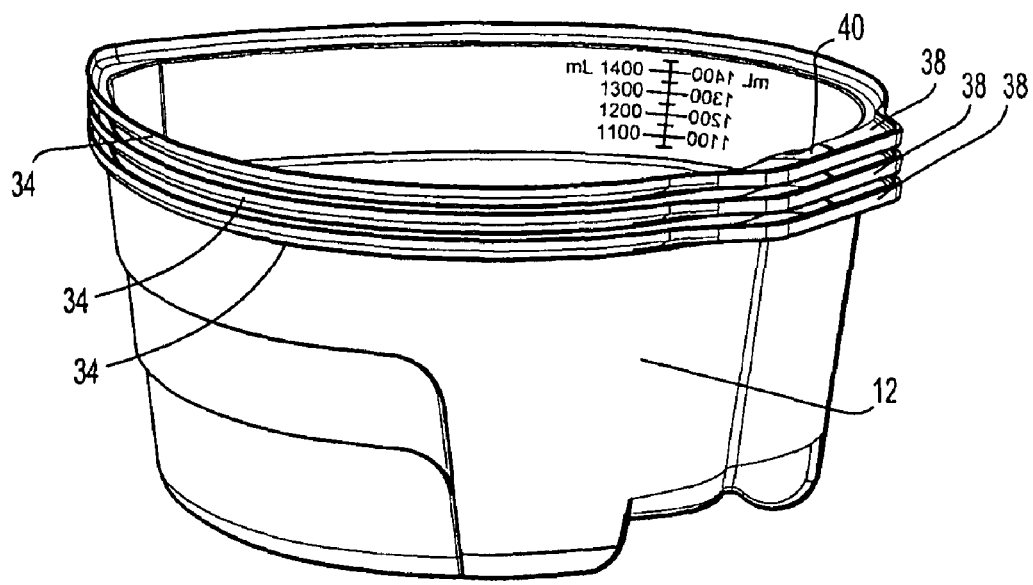
FIG. 7 is a perspective view illustrating three fluid basins of FIG. 1 nested within each other.
Figure 8:
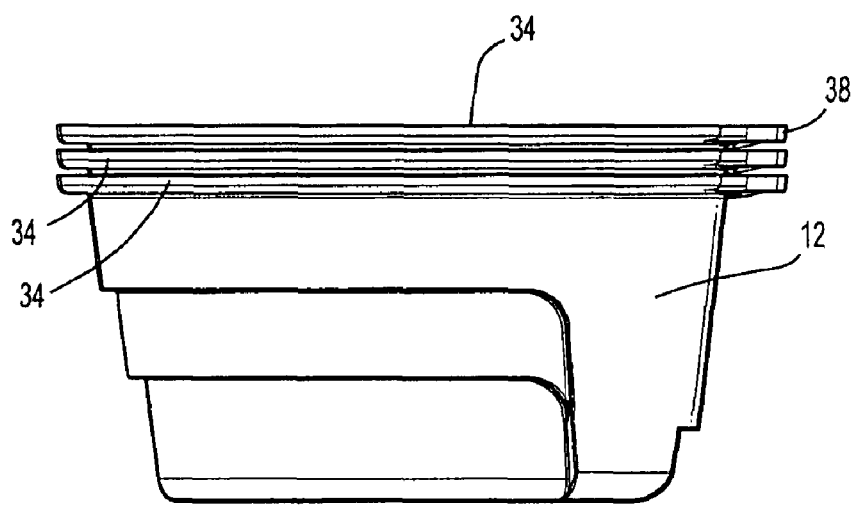
FIG. 8 is a side plan view of the three nested fluid basins.

FIGS. 7-8 illustrate a plurality of, e.g., three, fluid basins 10 nested or stacked within each other. The nested relation facilitates storage and/or transport of an inventory of fluid basins 10. In the nested relation, corresponding terraces 26, peripheral lips 34 and handle segments 38 of individual fluid basins 10 are in juxtaposed and, possibly, contacting relation. In addition, recesses 40 of handle segments 38 may be in superposed relation with adjacent recesses 40 nested within each other.

Figure 9:
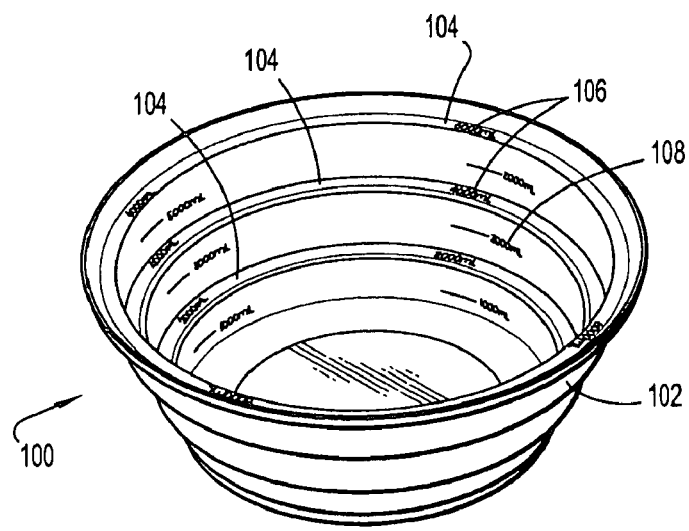
FIG. 9 is a perspective view of an alternate embodiment of the fluid basin incorporating a generally circular receptacle member.
Figure 10:
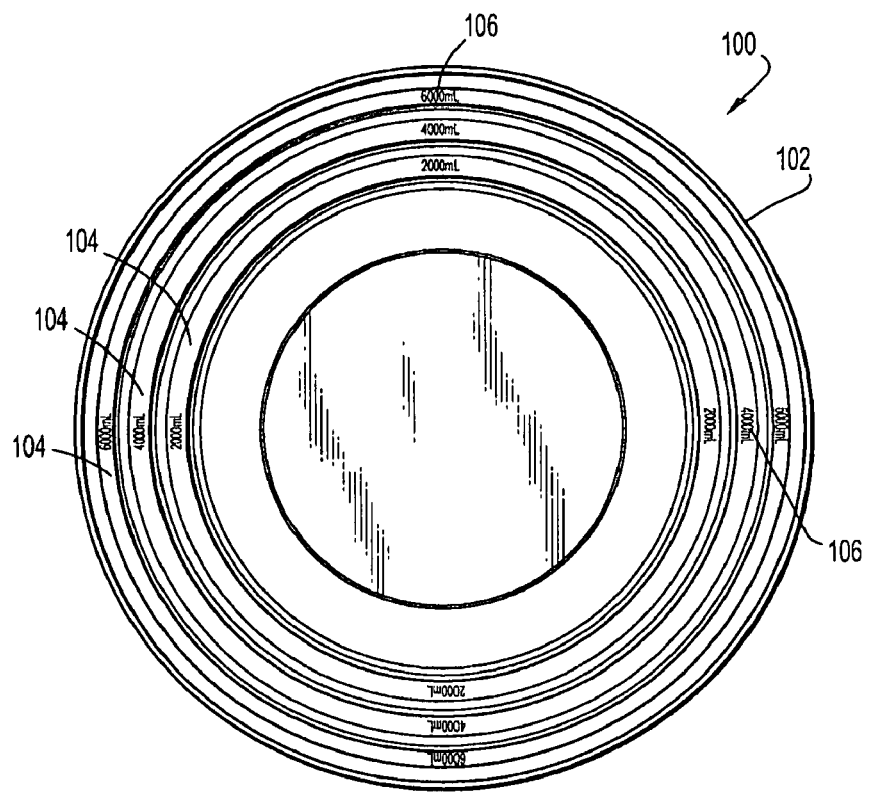
FIGS. 10 and 11 are top and side plan views respectively of the fluid basin of FIG. 9.
Figure 11:
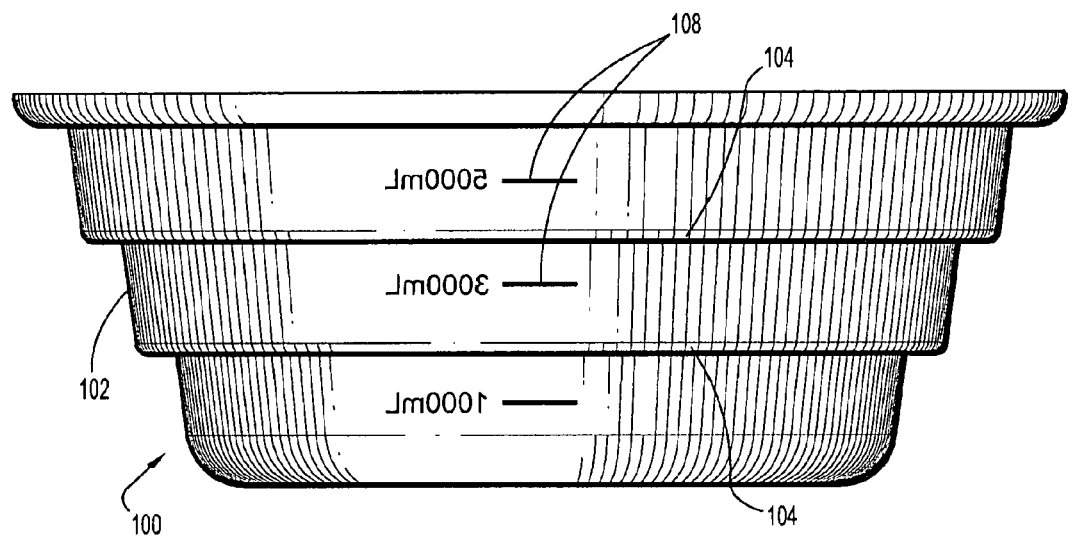

FIGS. 9-11 illustrate an alternate embodiment of the present disclosure. Fluid basin 100 defines a generally circular shape (when viewed from the top). Receptacle member 102 includes a plurality of terraces 104 which may extend around the entire perimeter of the receptacle member 102. Terraces 104 are dimensioned in a similar manner to terraces 26 of the embodiment of FIGS. 1-6. Indicia markings 106 may be positioned adjacent each terrace 104 to provide a quick and accurate determination of volume of fluid contained in receptacle member 102. Receptacle member 102 may have gradation markings 108 similar to gradation marks 46 of the embodiment of FIGS. 1-6 to provide a supplemental means to ascertain fluid volume within receptacle member 102. In most other respects, fluid basin 100 is similar to function to fluid basin 10 of FIGS. 1-6.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, surgical fluid basin may be circular, kidney, rectangular, or oblong shaped or any other shape. Terraces may extend about the entire periphery of receptable member. Other arrangements are also envisioned.

What is claimed is:

1. A surgical fluid basin apparatus, which comprises:
a receptacle member including a lower wall and a peripheral wall having an external wall surface and an internal wall surface opposite the external wall surface, the peripheral wall extending from the lower wall and arranged about a longitudinal axis, a cavity in general alignment with a handle segment, and having an internal chamber within the peripheral wall for reception of fluids, the peripheral wall having a plurality of terrace defined within the peripheral wall, each of the terraces corresponding to a volume of fluid contained within the internal chamber,
wherein each of the terraces defines an internal rise surface and an internal run surface intersecting the internal rise surface, each internal run surface including a central portion and side portions on opposite sides of the central portion, each side portion having a substantially uniform width that is less than a width of the central portion, and
wherein the internal run surface includes indicia markings corresponding to the volume of fluid contained within the internal chamber, and
said basin apparatus having a plurality of recessed wall surfaces that are located on the external wall surfaces of the basin apparatus, each of the plurality of recessed wall surfaces corresponding to the central portion of an internal run surface.

2. The surgical fluid basin apparatus according to claim 1 including a plurality of terraces defined within the peripheral wall, each terrace corresponding to a predetermined volume of fluid contained within the internal chamber.

3. The surgical fluid basin apparatus according to claim 1 wherein the peripheral wall includes an outer lip remote from the lower wall.

4. The surgical fluid basin apparatus according to claim 1 including secondary gradation markings on a wall surface of the peripheral wall and providing visual indicia regarding the volume of fluid in the container.

5. The surgical fluid basin apparatus according to claim 1 wherein the receptacle member is generally heart-shaped.

6. The surgical fluid basin apparatus according to claim 1 including first and second receptacle members, the first receptacle member adapted to receive the second receptacle member in nested relation.

7. The surgical fluid basin apparatus according to claim 1 wherein the handle segment is diametrically opposed to a cusp segment.

8. The surgical fluid basin apparatus according to claim 1 wherein the cavity is located in a lower wall.

* * * * *